United States Patent [19]

Hamilton et al.

[11] Patent Number: 5,381,799
[45] Date of Patent: Jan. 17, 1995

[54] INEXPENSIVE AND EASY TO USE MECHANICALLY OPERATED BITE FORCE GAUGE

[75] Inventors: Peter W. Hamilton, Cincinnati, Ohio; Gabriele B. Norado, Brookville, Ind.

[73] Assignee: The Procter & Gamble Company, Cincinnati, Ohio

[21] Appl. No.: 181,941

[22] Filed: Jan. 14, 1994

[51] Int. Cl.⁶ .................................................. A61B 5/103
[52] U.S. Cl. ................................................................ 128/777
[58] Field of Search ........................ 128/774, 777, 782; 606/205, 206; 33/511-514, 558.01, 558.2, 558.4

[56] References Cited

U.S. PATENT DOCUMENTS

| | | | |
|---|---|---|---|
| 2,773,308 | 12/1956 | Van Court et al. | 32/19 |
| 3,161,956 | 12/1964 | Van Court et al. | 32/19 |
| 3,297,021 | 1/1967 | Davis et al. | 128/2 |
| 4,204,326 | 5/1980 | Dimeff | 433/50 |
| 4,226,025 | 10/1980 | Wheeler | 33/512 |
| 4,324,547 | 4/1982 | Arcan et al. | 433/71 |
| 4,355,645 | 10/1982 | Mitani et al. | 128/777 |
| 4,390,028 | 6/1983 | Okano et al. | 128/777 |
| 4,402,326 | 9/1983 | Okano et al. | 128/774 |
| 4,488,873 | 12/1984 | Bloomfield et al. | 433/71 |
| 4,521,186 | 6/1985 | Wodlinger et al. | 433/71 |
| 4,541,803 | 9/1985 | Adler | 433/141 |
| 4,592,727 | 6/1986 | Bloomfield | 433/71 |
| 4,629,424 | 12/1986 | Lauks et al. | 433/6 |
| 4,734,034 | 3/1988 | Maness et al. | 433/68 |
| 4,786,254 | 11/1988 | Milstein et al. | 433/71 |
| 4,856,993 | 8/1989 | Maness et al. | 433/68 |
| 4,934,378 | 6/1990 | Perry, Jr. | 128/733 |
| 4,976,618 | 12/1990 | Anderson | 433/215 |
| 4,979,516 | 12/1990 | Abraham | 128/777 |
| 4,995,404 | 2/1991 | Nemir | 128/777 |
| 5,055,041 | 10/1991 | Eckland | 433/56 |
| 5,069,619 | 12/1991 | Frisbie | 433/72 |
| 5,078,153 | 1/1992 | Nordlander et al. | 128/777 |
| 5,156,161 | 10/1992 | Lollar | 606/205 |
| 5,158,096 | 10/1992 | Clark et al. | 128/777 |
| 5,190,051 | 3/1993 | Wilson | 128/777 |

FOREIGN PATENT DOCUMENTS 1468501 3/1988 U.S.S.R. ........................ 128/774

Primary Examiner—Max Hindenburg
Attorney, Agent, or Firm—Dean L. Garner

[57] ABSTRACT

In accordance with the present invention there is provided an easy to use mechanically operated bite force gauge for measuring the bite force at which a patient's dentures will begin to slip or dislodge within their mouth. The bite force two opposing beams each of which extends longitudinally between back and front ends. The beams are joined together by a back support column and by a bending support column. The bending support column defines, on each beam, a yielding member located between the two support columns and an extension member located between the bending support column and the front end. Thereafter, when biting forces are applied to the yielding members so that the two yielding members move towards each other, the extension members will move away from each other. The bite force gauge includes a force detector to measure the amount of force being applied to the yielding members by measuring the distance that the extension members move away from each other when the biting forces are applied.

7 Claims, 2 Drawing Sheets

INEXPENSIVE AND EASY TO USE MECHANICALLY OPERATED BITE FORCE GAUGE

FIELD OF THE INVENTION

The present invention relates to gnathodynamometers or bite force gauges for determining the biting force a patient is exerting with their teeth or dentures. The present invention has even further relation to such a gnathodynamometer which is mechanically operated and requires no expensive electrical, pneumatic or hydraulic components or the like. The present invention has even further relation to such gnathodynamometer which is easy to use and can be disposable.

BACKGROUND OF THE INVENTION

Many people wearing dentures today are unaware of the advantages of using a denture adhesive to better adhere their dentures to their gums. One way to demonstrate to a dentist or to a consumer the advantages of using a denture adhesive is to use what is referred to as a gnathodynamometer or a bite force gauge. A bite force gauge measures the amount of force exerted by the patient when they are biting down with their dentures. The bite force gauge can then be used to demonstrate the force at which it takes dentures to dislodge or slip when a denture adhesive is not being used and the force at which it takes dentures to slip when a denture adhesive is being used. Because the force at which the dentures slip will be much higher when a denture adhesive is used, the patient or dentist will quickly realize the benefits of using a denture adhesive. Therefore, gnathodynamometers are helpful for demonstrating the need for using denture adhesives.

However, many of the gnathodynamometers used in the past have been expensive machines having electrical devices and the like and are generally permanent in nature, therefore requiring the device to be sterilized between patients. This has been a large disadvantage in the commercialization of denture adhesives in that the manufacturers of denture adhesives are unwilling to give such expensive devices to dentists and the dentist is unwilling to go through the time and expense of sterilizing the device between each of his patients in order to show them the benefit of using a denture adhesive. In addition, the use of electrical strain gauges and the like require calibration and other expertise not readily available to a practicing Dentist. There has therefore been a need to provide a low cost gnathodynamometer which is easy to use, portable, and can be disposable.

SUMMARY OF THE INVENTION

In accordance with the present invention there is provided an easy to use mechanically operated bite force gauge. The bite force gauge has first and second opposing beams. Each of the beams extends along a longitudinal axis between back and front ends. The beams are joined together by a back support column, adjacent their back ends, and by a bending support column located between their front and back ends. The bending support column defines on each beam a yielding member located between the two support columns and an extension member located between the bending support column and the front end. Thereafter, when opposing forces are applied to the yielding members so that the two yielding members move towards each other, the extension members will move away from each other. The bite force gauge includes a force detector to measure the amount of force being applied to the yielding members by measuring the distance that the extension members move away from each other when the opposing forces are applied.

BRIEF DESCRIPTION OF THE DRAWINGS

While the specification concludes with claims particularly pointing out and distinctly claiming the subject matter forming the present invention it is believed the invention will be better understood from the following description of the preferred embodiment taken in conjunction with the accompanying drawings wherein:

DETAILED DESCRIPTION OF THE INVENTION

Figure 1:
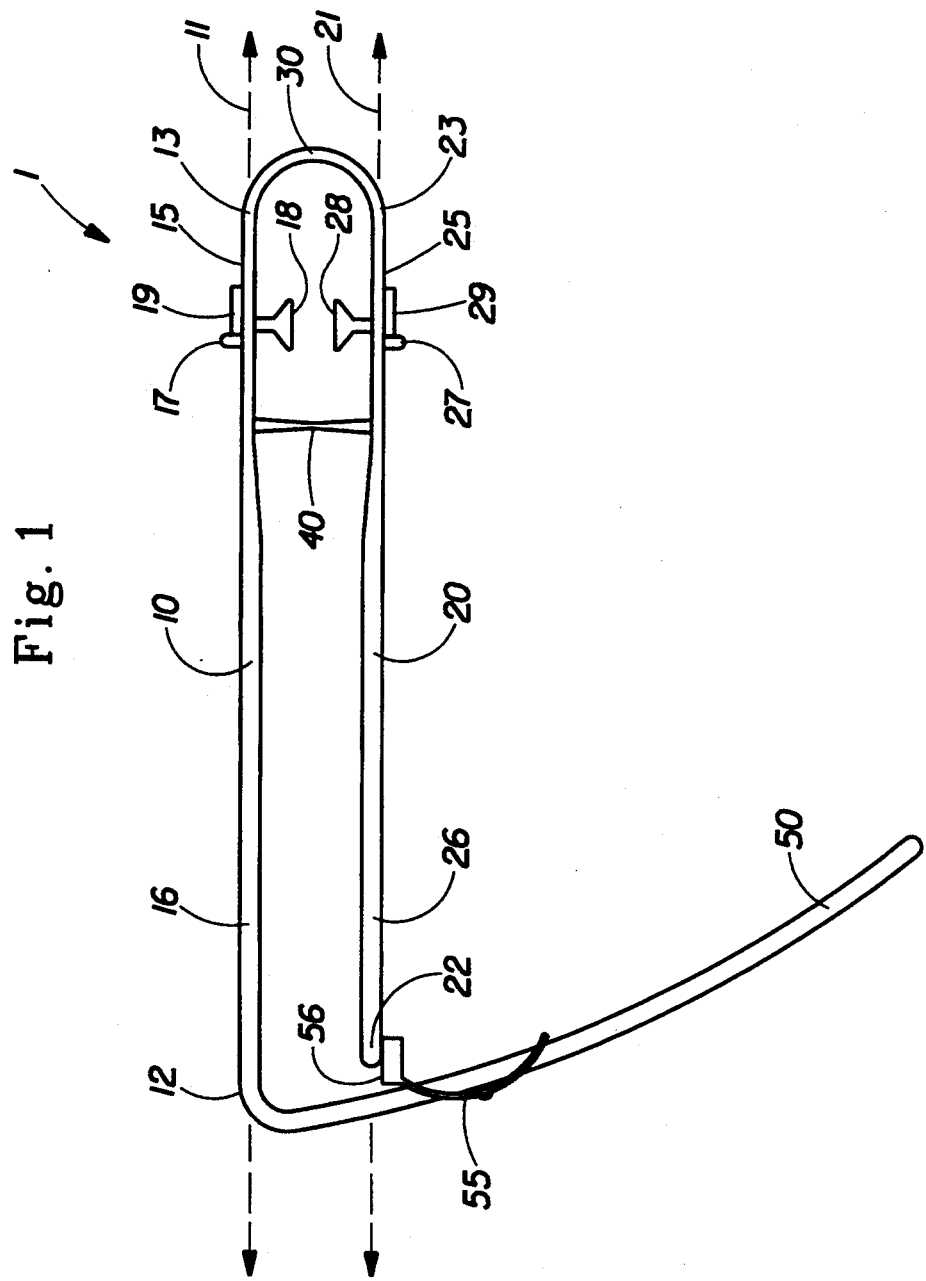
FIG. 1 is a side view of the bite force gauge of the present invention.

Referring to the drawings in detail wherein like numerals indicate the same element throughout the view there is shown in FIG. 1 a bite force gauge 1 for measuring bite force. The bite force gauge comprises first and second opposing beams 10 and 20, respectively. Although FIG. 1 shows beams 10 and 20 as being parallel, they need not be. The first beam 10 extends along a longitudinal axis 11 between front and back ends 12 and 13, respectively. Similarly, second beam 20 extends along a longitudinal axis 21 between front and back ends 22 and 23, respectively. Beams 10 and 20 are joined together, adjacent their back ends 13 and 23, by a back support column 30. Back support 30 is shown in the figures as being a curved hinge. However, the back support need not be curved and need not be at the extreme portion of the back ends. Beams 10 and 20 are also joined together by bending support column 40, located between back support column 30 and front ends 12,22. Bending support column 40 thereby defines a yielding member and an extension member on each beam. Beam 10 includes yielding member 15 between the two support columns 30 and 40 and an extension member 16 located between bending support column 40 and front end 12. Similarly, beam 20 includes yielding member 25 between the two support columns 30 and 40 and an extension member 26 located between bending support column 40 and front end 22.

Figure 2:
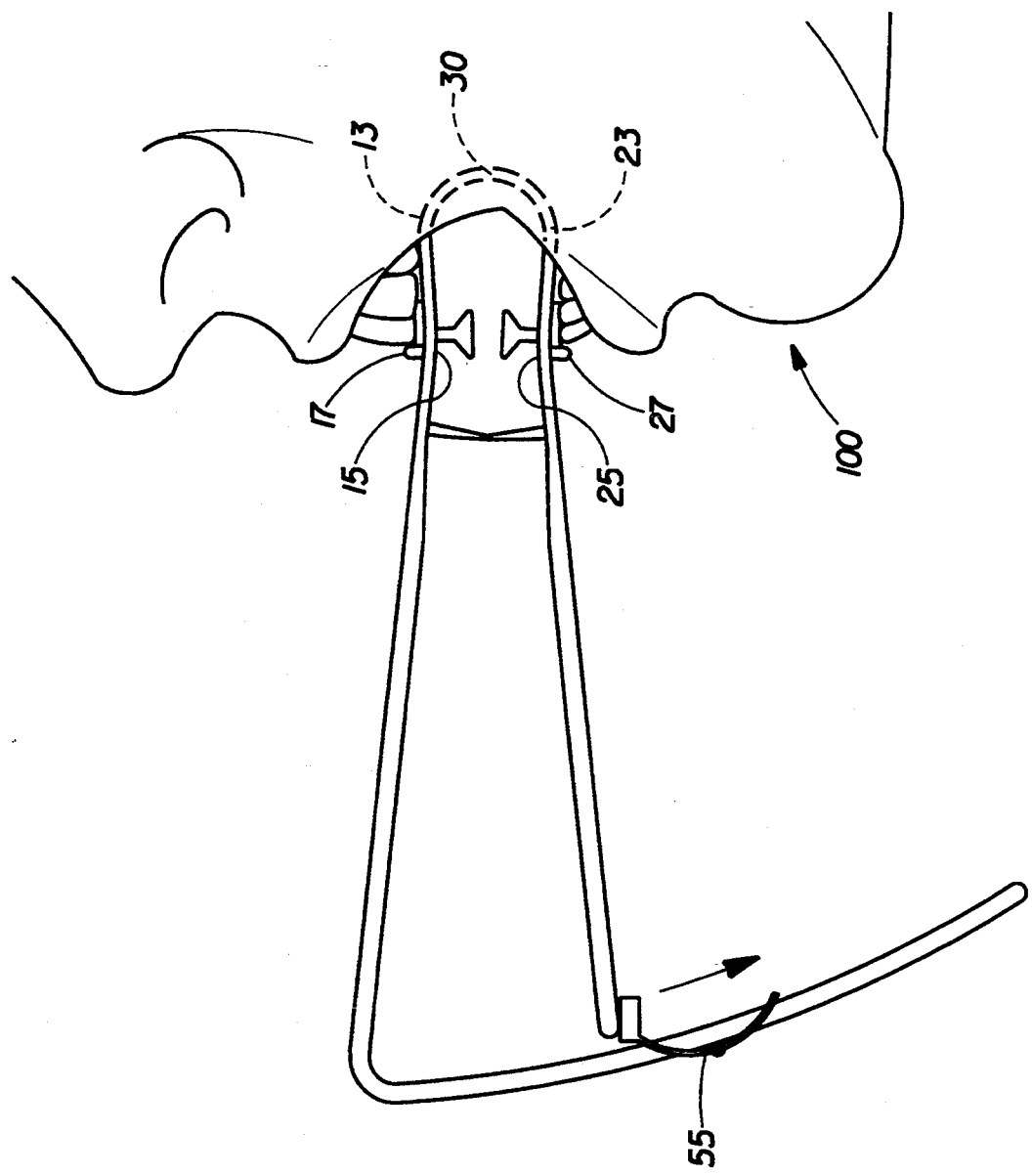
FIG. 2 is a view figure similar to FIG. 1 showing a bite force in use.

How the above described components of bite gauge work in order to determine the bite force at which a patients dentures will slip can best be described by referring to FIG. 2. FIG. 2 is a view similar to FIG. 1 but shows a patient 100 using the bite gauge. As seen from the figure a patient will insert the gauge into their mouth near back ends 13 and 23. The patient will then bite down on the two yielding members 15 and 25 at a predetermined point. In the present embodiment, the predetermined points at which the patient is supposed to bite is noted by teeth stops 17 and 27, which are merely small outwardly disposed projections. Furthermore, pads 19 and 29, preferably made from closed cell polyethylene foam, are placed before stops 17 and 27 to provide comfort and stability for the user. The front of the patient's teeth should abut against teeth stops 17 and 27 and should be resting on pads 19 and 29, thereby telling the patient where they should bit down. Once the patient begins to bite on yielding members 15 and 25 the yielding members begin to move toward each other and the extension members 16 and 26 begin to move away from each other. The preferred design of the gauge shown in the Figures has a low stress and yielding potential so that the patient can bite on yielding members until they touch each other, without worry of any plastic deformation to the gauge.

Thereafter, by knowing the dimensions and materials that beams and support columns are made from, the positions of the support columns and the position of the teeth stops the bite force exerted by the patient can be determined by measuring the distance that the two extension members move away from each other. Therefore, the gauge preferable includes a means for measuring the distance the two beams moved apart. This could be done by holding up a ruler to the front ends 12 and 22 and measuring the distance they move apart from each other.

Preferably, in order to measure the bite force, the bite force gauge 1 further includes a force detector which measures the amount of force being applied to the yielding members 15 and 25 by measuring the distance that the extension members 16 and 26 move away from each other. For the embodiment shown in FIGS. 1 and 2 the force detector comprises force scale arm 50. Force scale arm 50 extends downwardly from beam 10 towards beam 20. The force detector further includes a follower 55 which is slidingly engaged with scale arm 50 and preferably has low friction contact therewith. Follower 50 has platform 56 which makes contact with extension member 26. As the patient begins to bite down on yielding members 15 and 25, and extension members 16 and 26 begin to move away from each other, extension member 26 will make contact with platform 56 of follower 55 and begin to move the follower down the scale arm 50. After the patients dentures have slipped and they stop biting the distance that the extension members moved away from each other can be determined by measuring the distance that the follower moved along the scale arm 50. Therefore, the bite force can be measured by measuring the distance that the follower traveled down scale arm 50 from some starting point on scale arm 50. This is easily accomplished by placing a marked scale on the outside of scale arm 50. The zero point, or starting point, for the follower could be the point along the scale arm aligned with longitudinal axis 21 of beam 20 when the gauge 1 is at rest, i.e. has no bite force exerted on it. Before biting the follower should then be placed directly under beam 20.

In a preferred embodiment gauge I further includes deflection stops 18 and 28. Deflection stop 18 projects downwardly from beam 10 towards beam 20. Deflection stop 28 projects upwardly from beam 20 towards beam 10. These deflection stops prevent the yielding of members 15 and 25, beyond their maximum design deflection. This prevents plastic deformation of the beams which could cause inaccurate force readings during subsequent testing. In order for the patient to be comfortable when placing the gauge in their mouths, the distance between the teeth stops 17 and 27 and back support column 30 is preferably no more than one inch (2.54 cm.) and the outside distance between beams 10 and 20 is no more than ¾ of an inch (1.905 cm.).

In one preferred embodiment the gauge 1 is formed from a single piece of injection molded polycarbonate wherein the thickness of beams 10 and 26 is about 0.075 inches (0.1905 cm.). The distance of the teeth stops 17 and 27 to back support column 30 is preferably about 1 inch (2.54 cm.). The distance between bending support beam 40 and back support column 30 is preferably about 1.5 inches (3.810 cm.). The length of beam 10 between the front end and the back support column is preferably about 5.085 inches (12.916 cm.) and the length of beam 20 between the front end and the back support column is about 4.98 inches (12.649 cm.). The beam is preferably designed so that a maximum amount of three placed on the yielding members is about 20 lbs. and if yielding members 15 and 25 move together ¼ inch (0.635 cm.) front ends 12 and 22 of beams 10 and 20 will move apart 2 inches (5.08 cm.).

While particular embodiments of the present invention have been illustrated and described various modifications will be apparent to those skilled in the art without departing from the spirit and scope of the present invention. Accordingly, the scope of the present invention should be considered in terms of the following claims and is understood not to be limited to the details described and shown in the specification and drawings.

What is claimed is:

1. An easy to use mechanically operated bite force gauge, said bite force gauge comprising:
   (a) first and second opposing beams, each of said beams extending along a longitudinal axis between back and front ends, said beams being joined together by a back support column, adjacent their back ends, and by a bending support column located between back support column and said front ends;
   (b) said bending support column thereby defining on each beam a yielding member located between said two support columns, and an extension member located between said bending support column and said front end, whereby when opposing forces are applied to said yielding members by a patient's teeth so that said two yielding members move toward each other, said extension members will move away from each other; and
   (c) a force detector to measure the amount of said force being applied to said yielding members by measuring the distance said extension members move away from each other when said opposing forces are applied.

2. The bite force gauge of claim 1 wherein said force detector comprises:
   (a) a force scale arm extending from said front end of said first beam, said force scale arm extending downwardly from said first beam towards said second beam; and
   (b) a follower slidingly engaged with said force scale arm, said follower having a platform on which said front end of said second beam is able to abut against, whereby when said opposing forces are applied to said bite force gauge and said extension members move away from each other, said second beam moves down along said force scale arm and measures the distance said extension members moved away from each other and hence measures magnitude of said opposing forces.

3. The bite force gauge of claim 1 wherein said beams each have a deflection stop between said two supporting columns, said deflection stops being opposing and facing each other so as to prevent permanent deflection of said yielding members.

4. The bite force gauge of claim 1 wherein said each of said yielding members includes an outwardly projecting teeth stop so as to indicate to the patient where to bite on said gauge.

5. The bite force gauge of claim 2 wherein each of said yielding members further includes a pad before said teeth stops.

6. The bite force gauge of claim 1 wherein said gauge is formed from a single piece of polycarbonate.

7. An easy to use mechanically operated bite force gauge, said bite force gauge comprising:
(a) first and second opposing beams, each of said beams extending along a longitudinal axis between back and front ends, said beams being joined together by a back support column, adjacent their back ends, and by a bending support column located between said back support column and said front ends;
(b) said bending support column thereby defining on each beam a yielding member located between said two support columns, and an extension member located between said bending support column and said front end, whereby when opposing forces are applied to said yielding members by a patient's teeth so that said two yielding members move toward each other, said extension members will move away from each other; and
(c) a means for measuring the distance said extension members move away from each other when said opposing forces are applied.

* * * * *

UNITED STATES PATENT AND TRADEMARK OFFICE
CERTIFICATE OF CORRECTION

PATENT NO. : 5,381,799

DATED : January 17, 1995

INVENTOR(S) : Peter W. Hamilton et al.

It is certified that error appears in the above-identified patent and that said Letters Patent is hereby corrected as shown below:

Column 3, line 36, after "biting" insert -- , -- .

Column 3, line 49, "gauge I" should read -- gauge 1 -- .

Column 4, line 7, "three" should read -- force -- .

Signed and Sealed this

Fourteenth Day of April, 1998

*Attest:*

BRUCE LEHMAN

*Attesting Officer*   *Commissioner of Patents and Trademarks*